US012376798B2

(12) United States Patent
Kim et al.

(10) Patent No.: US 12,376,798 B2
(45) Date of Patent: Aug. 5, 2025

(54) CONTROL STICK FOR MILITARY AIRCRAFT

(71) Applicant: Defense Agency for Technology and Quality, Gyeongsangnam-do (KR)

(72) Inventors: Tae Hwan Kim, Gyeongsangnam-do (KR); Sang Woo Noh, Gyeongsangnam-do (KR); Jin Woo Ahn, Gyeongsangnam-do (KR)

(73) Assignee: Defense Agency for Technology and Quality, Gyeongsangnam-do (KR)

( * ) Notice: Subject to any disclaimer, the term of this patent is extended or adjusted under 35 U.S.C. 154(b) by 355 days.

(21) Appl. No.: 18/031,646

(22) PCT Filed: Oct. 13, 2020

(86) PCT No.: PCT/KR2020/013920
§ 371 (c)(1),
(2) Date: Apr. 13, 2023

(87) PCT Pub. No.: WO2022/080512
PCT Pub. Date: Apr. 21, 2022

(65) Prior Publication Data
US 2023/0384817 A1 Nov. 30, 2023

(30) Foreign Application Priority Data
Oct. 13, 2020 (KR) ........................ 10-2020-0131778

(51) Int. Cl.
*A61B 5/00* (2006.01)
*A41D 19/00* (2006.01)
(Continued)

(52) U.S. Cl.
CPC ........ *A61B 5/6897* (2013.01); *A41D 19/0027* (2013.01); *A61B 5/02055* (2013.01);
(Continued)

(58) Field of Classification Search
CPC ... A61B 5/6897; A61B 5/02055; A61B 5/318; A61B 5/6806; A61B 5/02438;
(Continued)

(56) References Cited

U.S. PATENT DOCUMENTS 5,283,643 A * 2/1994 Fujimoto ............... B64D 45/00
381/384
5,472,156 A 12/1995 Bivens, III et al.
(Continued)

FOREIGN PATENT DOCUMENTS

CN 204950933 1/2016
JP 07-096897 4/1995
(Continued)

OTHER PUBLICATIONS

Notice of Reasons for Rejection Dated Mar. 26, 2024 From the Japan Patent Office Re. Application No. 2023-52618 and Its Translation Into English. (13 Pages).
(Continued)

*Primary Examiner* — Jonathan T Kuo (57) ABSTRACT

The present application relates to a control stick for a military aircraft, a system for managing health information regarding a pilot, a military aircraft, and a simulator for a military aircraft. According to the control stick for a military aircraft, the system for managing health information regarding a pilot, the military aircraft, the military aircraft, and the simulator for a military aircraft of the present application, health information regarding a pilot may be continuously monitored, and flight accidents such as personal damage and material damage may be prevented via the collection of the health information.

23 Claims, 8 Drawing Sheets

(51) Int. Cl.
*A61B 5/0205* (2006.01)
*A61B 5/024* (2006.01)
*A61B 5/318* (2021.01)
*B64C 13/04* (2006.01)
*B64D 45/00* (2006.01)

(52) U.S. Cl.
CPC ............ *A61B 5/318* (2021.01); *A61B 5/6806* (2013.01); *B64C 13/0421* (2018.01); *B64D 45/00* (2013.01); *A61B 5/02438* (2013.01); *A61B 2503/22* (2013.01); *B64D 2045/0065* (2013.01)

(58) Field of Classification Search
CPC . A61B 2503/22; A61B 5/0006; A61B 5/0008; A61B 5/225; A61B 5/01; A61B 5/02444; A61B 5/6825; A61B 5/6898; A61B 5/024; A61B 5/6887; A61B 2503/12; A41D 19/0027; A41D 19/015; B64C 13/0421; B64D 45/00; B64D 2045/0065; G05G 2009/04774; G05G 9/047; G09B 9/165
See application file for complete search history.

(56) References Cited

U.S. PATENT DOCUMENTS

| | | | |
|---|---|---|---|
| 7,145,477 B1 | 12/2006 | McBain | |
| 7,155,034 B1* | 12/2006 | Recce | F41A 17/066 |
| | | | 382/218 |
| 11,554,853 B2* | 1/2023 | Lampazzi | G05G 1/01 |
| 2006/0285725 A1* | 12/2006 | Recce | E05F 15/695 |
| | | | 340/5.52 |
| 2021/0070427 A1* | 3/2021 | Lampazzi | G05G 1/01 |

FOREIGN PATENT DOCUMENTS

| | | |
|---|---|---|
| KR | 10-20130123055 | 11/2013 |
| KR | 10-2018-0094553 | 8/2018 |
| KR | 10-2019-0071243 | 6/2019 |

OTHER PUBLICATIONS

International Search Report and the Written Opinion Dated Jul. 8, 2021 From the International Searching Authority Re. Application No. PCT/KR2020/013920 and Its Translation of Search Report Into English. (11 Pages).
Falconpedia "Hands-On Throttle and Stick", Falconpedia, Wikidot, 4 P., Last Edited Sep. 14, 2011.

* cited by examiner

CONTROL STICK FOR MILITARY AIRCRAFT

RELATED APPLICATIONS

This application is a National Phase of PCT Patent Application No. PCT/KR2020/013920 having International filing date of Oct. 13, 2020, which claims the benefit of priority of Republic of Korea Patent Application No. 10-2020-0131778 filed on Oct. 13, 2020. The contents of the above applications are all incorporated by reference as if fully set forth herein in their entirety.

FIELD AND BACKGROUND OF THE INVENTION

The present application relates to a military aircraft control stick, a health information management system for a pilot, a military aircraft, and a military aircraft simulator.

Pilots, particularly, fighter pilots, frequently find themselves in harsh environments according to the situation. Accordingly, when the minds and bodies of the pilots are not stable, expensive aircrafts as well as themselves may be seriously damaged.

In the related art, an image input using a camera is provided to a display device of a manager, and the manager may identify a state of the pilot on the basis of the provided image. However, the manager cannot help determining the state of the pilot only on the basis of subjective determination of the manager.

Further, in the related art, since only a black box is present, only a situation after an accident may be determined, but a state of the pilot may not be identified in advance.

Thus, in order to solve this problem, a health information management system using a control stick, which is a device always used by a pilot, is required to continuously monitor a health state of the pilot.

SUMMARY OF THE INVENTION

The present invention is directed to providing a military aircraft control stick, a health information management system for a pilot, a military aircraft, and a military aircraft simulator, which may continuously monitor health information of the pilot, collect the health information, and thus prevent flight accidents such as human damages and property damages.

One aspect of the present invention provides a military aircraft control stick including an attitude control unit and an engine thrust control unit, each of the attitude control unit and the engine thrust control unit including a detection module that detects a biometric information of a pilot, a reception module that receives the biometric information detected by the detection module, and a transmission module that transmits the biometric information received by the reception module to a flight recorder.

The attitude control unit may include a trim switch, a camera control switch, an armament launch and drop switch, a missile step nosewheel switch, a screen display control switch, a paddle switch, a pinky switch, a target designation or selection switch, and a trigger.

The attitude control unit may include a detection module that detects biometric information including a heart rate and a pressure.

In the attitude control unit, the detection module that detects the heart rate may be provided at a lower end of a side surface opposite to a side surface adjacent to the pilot.

In the attitude control unit, the detection module that detects the pressure may be provided at a center of a side surface opposite to a side surface adjacent to the pilot.

The attitude control unit may further include a detection module that detects one or more pieces of biometric information selected from the group consisting of an electrocardiogram and a temperature.

In the attitude control unit, the detection module that detects the electrocardiogram may be provided at one or more of the trigger and a lower end of a side surface adjacent to the pilot.

In the attitude control unit, a module that detects the temperature may be provided at an upper end of a side surface adjacent to the pilot.

The engine thrust control unit may include an antenna elevation switch, a communication switch, a speed brake switch, a manual range or uncaging switch, and a dog fight or missile switch.

The engine thrust control unit may include a detection module that detects one or more pieces of biometric information selected from the group consisting of an electrocardiogram, a temperature, a pressure, and a heart rate.

In the engine thrust control unit, the detection modules that detect the electrocardiogram, the temperature, and the pressure may be sequentially provided on a side surface adjacent to the pilot.

In the engine thrust control unit, a detection module that detects the heart rate may be provided at a lower end of a side surface opposite to a side surface adjacent to the pilot.

The reception module may be provided adjacent to the detection module that is provided in the attitude control unit or the engine thrust control unit and detects the electrocardiogram.

The reception module may directly receive a signal generated by the detection module without conversion into a different signal.

The transmission module may include a connection cable that connects the military aircraft control stick to the flight recorder.

The transmission module may transmit the received biometric information to the flight recorder according to a 1553 communication protocol.

The military aircraft control stick may further include a power module that applies power to the detection module, the reception module, and the transmission module.

A health information management system for a pilot of the present application may use the military aircraft control stick.

The health information management system for the pilot may further include a control glove that allows a hand of a pilot to come into direct contact with the military aircraft control stick.

The control glove may have conductive fiber pads attached to a palm surface and a knuckle surface adjacent to the palm surface to transmit a microcurrent of the pilot's skin.

The control glove may further have transparent pads attached to knuckle surfaces of fingertips to measure a heart rate using a blood flow of a finger.

Another aspect of the present invention provides a military aircraft according to the present application including the military aircraft control stick.

Still another aspect of the present invention provides a military aircraft simulator according to the present application including the military aircraft control stick.

According to a military aircraft control stick, a health information management system for a pilot, a military aircraft, and a military aircraft simulator of the present application, health information of the pilot is continuously monitored, the health information is collected, and thus flight accidents such as human damages and property damages can be prevented.

DESCRIPTION OF SPECIFIC EMBODIMENTS OF THE INVENTION

Hereinafter, a military aircraft control stick according to the present application will be described with reference to the accompanying drawings, the accompanying drawings are illustrative, and the military aircraft control stick according to the present application is not limited to the accompanying drawings.

Figure 1:
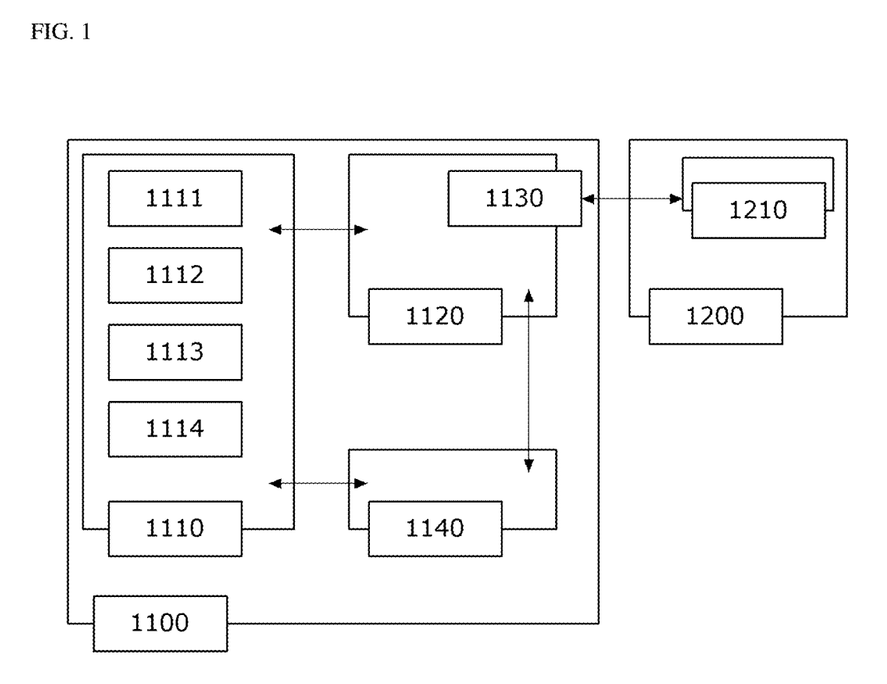
FIG. 1 is a diagram illustrating a military aircraft control stick according to an embodiment of the present application for transmitting biometric information of a pilot to a flight recorder.

FIG. 1 is a diagram illustrating a military aircraft control stick according to an embodiment of the present application for transmitting biometric information of a pilot to a flight recorder. As illustrated in FIG. 1, a military aircraft control stick 1100 according to the present application for transmitting data to a flight recorder 1200, which is a control stick using a hands-on-throttle and stick (HOTAS) method, includes an engine thrust control unit (not illustrated) and an attitude control unit (not illustrated), and the engine thrust control unit or the attitude control unit includes a detection module 1110, a reception module 1120, and a transmission module 1130. The military aircraft control stick according to the present application may continuously monitor health information of the pilot and can prevent accidents such as human damages and property damages through the collection of the health information.

Figure 2:
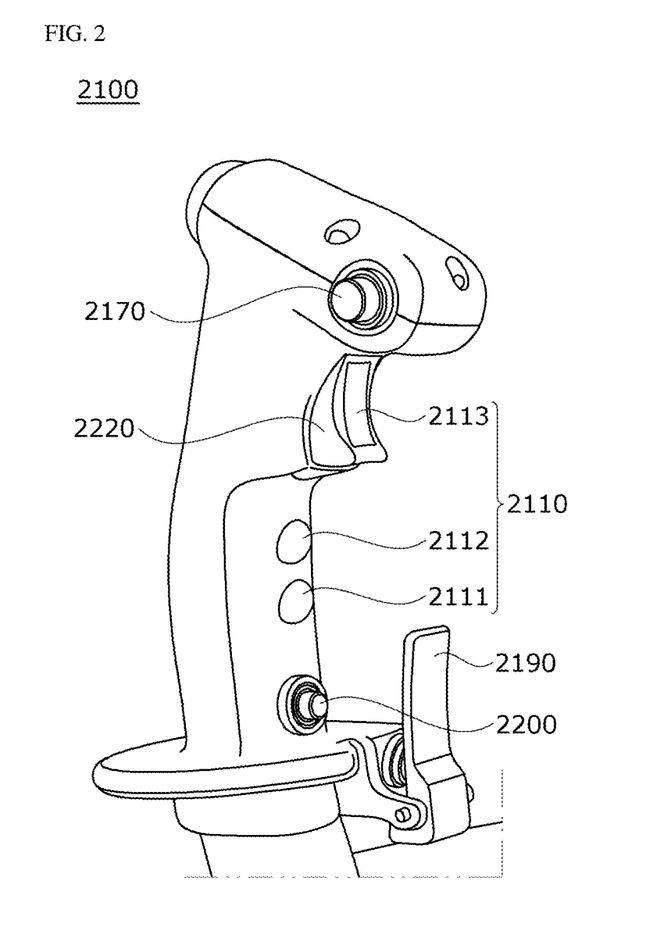
FIG. 2 is a view illustrating a side opposite to a side of an attitude control unit, which is adjacent to the pilot, according to an embodiment of the present application.
Figure 3:
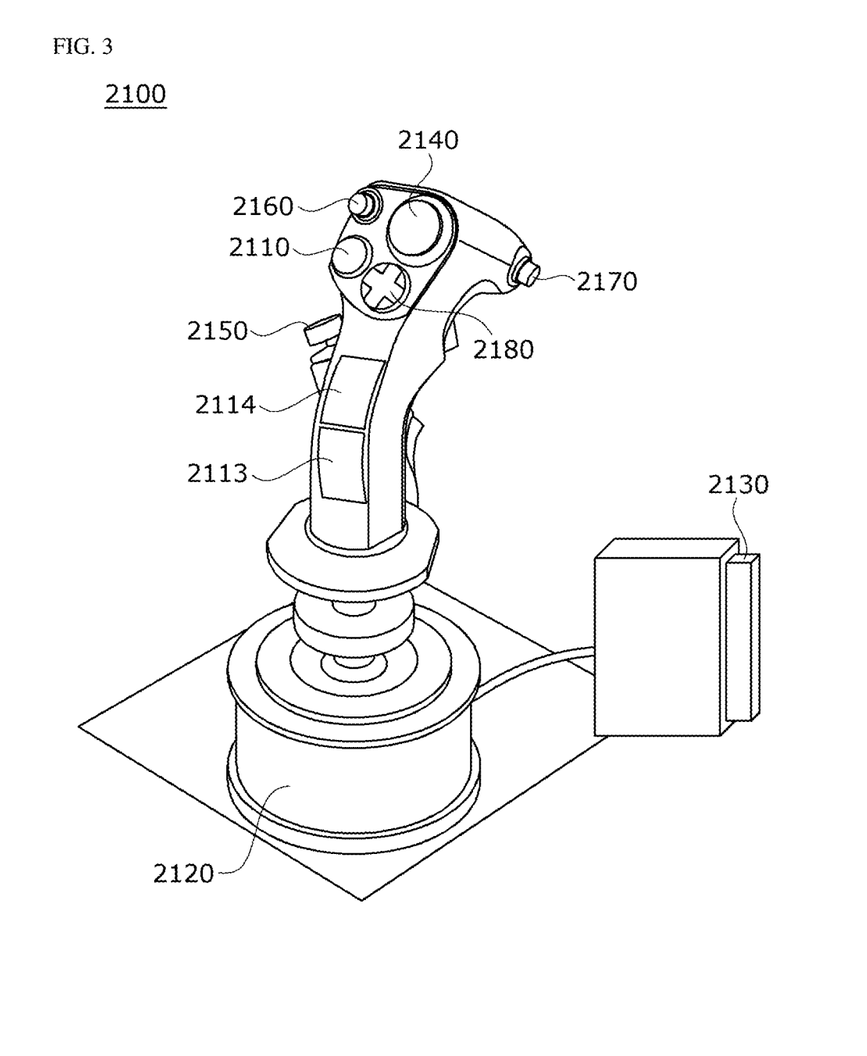
FIG. 3 is a view illustrating the side surface adjacent to the pilot of the attitude control unit according to an embodiment of the present application.

The attitude control unit is a rod-shaped device for controlling a flight direction and a movement direction of a military aircraft. FIG. 2 is a view illustrating a side opposite to a side of an attitude control unit, which is adjacent to the pilot, according to an embodiment of the present application. FIG. 3 is a view illustrating the side surface adjacent to the pilot of the attitude control unit according to an embodiment of the present application. As illustrated in FIGS. 2 and 3, the attitude control unit 2100 may include a trim switch 2140, a camera control switch 2150, an armament launch and drop switch 2160, a missile step nosewheel switch 2170, a screen display control switch 2180, a paddle switch 2190, a pinky switch 2200, a target designation or selection switch 2210, and a trigger 2220.

The trim switch is a four-way push switch and may adjust a pitch attitude and a roll attitude of the military aircraft. Further, the four-way push switch may be operated by being pushed upward, downward, leftward, or rightward, and may be automatically restored when a hand is detached.

Further, the camera control switch is a trim-type switch that controls a camera of the military aircraft that performs an acrobatic maneuver and may control a photographing direction by physically rotating the camera.

Further, the armament launch and drop switch is an armament drop control switch and may drop a missile during an air-to-ground armament mission.

Further, the missile step nosewheel switch is a front wheel steering device and missile selection switch of the military aircraft, may control a front wheel steering device when the switch is pressed on the ground before flight, and may perform a missile launch function when the switch is pressed in the air during the flight.

Further, the screen display control switch is an in-cockpit multi-function screen display control switch and may perform various display options and display selections.

Further, the trigger is a machine gun firing switch and may operate a machine gun when clicked.

The detection modules 1110 and 2110 are components that detect biometric information of an aircraft pilot. The detection module may be provided in the military aircraft control stick, for example, the attitude control unit and/or the engine thrust control unit, and thus acquire the biometric information of the pilot.

In an example, the attitude control unit may include a detection module for detecting the biometric information including a heart rate and a pressure.

Figure 4:
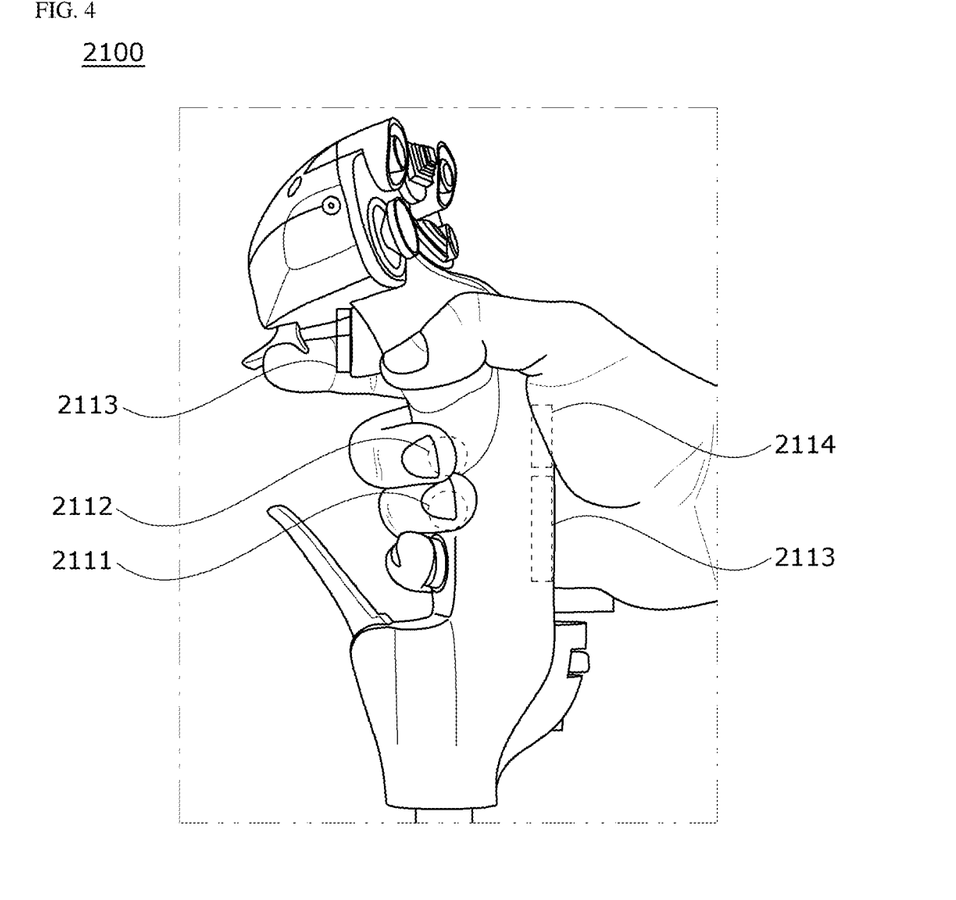
FIG. 4 is a captured image for describing a detection module in contact with a hand of the pilot when the pilot grips the attitude control unit according to an embodiment of the present application.

The heart rate is a number of heart beats. The heart rate may be measured using a finger blood flow of the pilot. For example, in the attitude control unit, detection modules 1111 and 2111 for detecting the heart rate may be provided at a lower end of a side surface opposite to a side surface adjacent to the pilot. FIG. 4 is a captured image for describing a detection module in contact with a hand of the pilot when the pilot grips the attitude control unit according to an embodiment of the present application. As illustrated in FIG. 4, the module 2111 for detecting the heart rate may be provided at a portion at which a ring finger of the pilot is positioned when the control stick is gripped. Accordingly, the health information of the pilot may be continuously monitored, the health information may be collected, and thus flight accidents such as human damages and property damages can be prevented.

The pressure is a force for gripping the above-described control stick using a hand and may be expressed as a gripping force. The pressure may be measured when the above-described control stick is gripped. For example, in the attitude control unit, detection modules 1112 and 2112 for detecting the pressure may be provided at a center of the side surface opposite to the side surface adjacent to the pilot. In detail, as illustrated in FIG. 4, the module 2112 for detecting the pressure may be provided at the portion at which the ring finger of the pilot is positioned when the control stick is gripped. Accordingly, the health information of the pilot may be continuously monitored, the health information may be collected, and thus flight accidents such as human damages and property damages can be prevented.

In still another example, the attitude control unit may further include a detection module for detecting one or more pieces of biometric information selected from the group consisting of an electrocardiogram and a temperature.

The electrocardiogram means that an action current according to contraction of a heart is recorded as a curved line. The electrocardiogram may be measured using a skin conductivity and a pulse rate of the pilot. For example, in the attitude control unit, detection modules 1113 and 2113 for detecting the electrocardiogram may be provided at one or more of the trigger and the lower end of the side surface adjacent to the pilot. In detail, as illustrated in FIG. 4, the detection module 2113 for detecting the electrocardiogram may be provided at one or more of the trigger at which an index finger of the pilot is positioned and a lowermost end of a portion at which a palm of the pilot is positioned when the control stick is gripped. Accordingly, the health information of the pilot may be continuously monitored, the health information may be collected, and thus flight accidents such as human damages and property damages can be prevented.

The temperature is a body temperature of the pilot. The temperature may be measured using a skin temperature of the pilot. For example, in the attitude control unit, detection modules 1114 and 2114 for detecting the temperature may be provided at an upper end of the side surface adjacent to the pilot. In detail, as illustrated in FIG. 4, the module 2114 for detecting the temperature may be provided above the detection module for detecting the electrocardiogram among a portion at which the palm of the pilot is positioned when the control stick is gripped. Accordingly, the health information of the pilot may be continuously monitored, the health information may be collected, and thus flight accidents such as human damages and property damages can be prevented.

Figure 5:
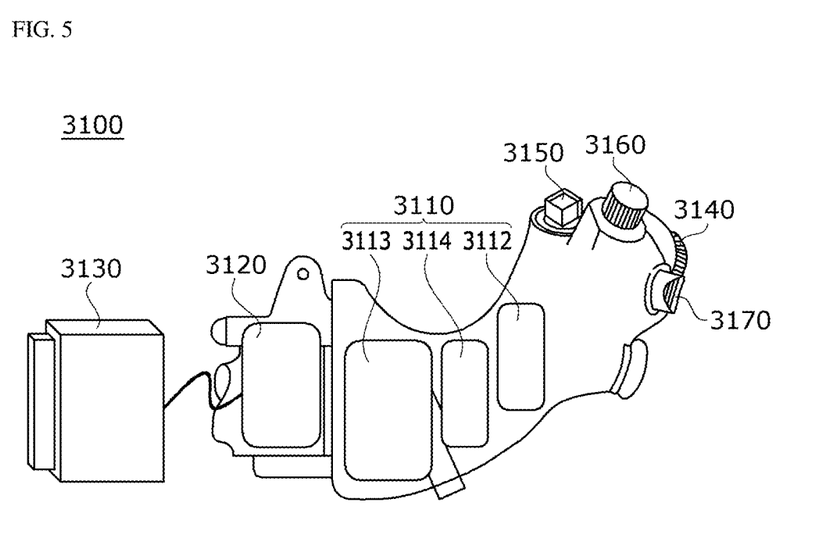
FIG. 5 is a view illustrating a side opposite to a side of an engine thrust control unit, which is adjacent to the pilot, according to an embodiment of the present application.

The engine thrust control unit is a rod-shaped device that controls a thrust adjustment function, a fight-back function, and a flight control function of the military aircraft. FIG. 5 is a view illustrating a side opposite to a side of an engine thrust control unit, which is adjacent to the pilot, according to an embodiment of the present application. As illustrated in FIG. 5, the engine thrust control unit 3100 may include an antenna elevation switch 3140, a communication switch 3150, a speed brake switch (not illustrated), a manual range or uncaging switch 3160, and a dog fight or missile switch 3170.

The antenna elevation switch is a radar control switch and may physically control an attitude of a mechanical radar upward, downward, leftward, or rightward to scan a target in a desired direction.

Further, the communication switch is a transmission channel operation switch and may perform communication by selecting an ultra-high frequency (UHF)/very high frequency (VHF) channel. The UHF channel is an ultra-short wave channel using wireless electromagnetic waves having a wavelength range of 1 mm to 1 m and a frequency allocated between 300 MHz to 3.0 GHz. The VHF channel is a very short wave channel using wireless electromagnetic waves having a wavelength range of 1 m to 10 m and a frequency allocated between 30 MHz to 300 MHz.

Further, the speed brake switch is a speed reducer operation switch and may reduce a planning speed and rapidly reduce a speed during flight.

Further, the manual range/uncaging switch is a switch for manually setting a radar range and activating and operating a video of a guided missile and may operate a tracking camera by manually setting the radar range or removing a dome cover of the guided missile in an air-to-air machine gun mode.

Further, the dogfight/missile switch is a dogfight or missile override mode selection switch and may select a machine gun firing mode or an air-to-air missile launch mode.

In an example, the engine thrust control unit may include a detection module 3110 that detects one or more pieces of biometric information selected from the group consisting of an electrocardiogram, a temperature, a pressure, and a heart rate.

Figure 6:
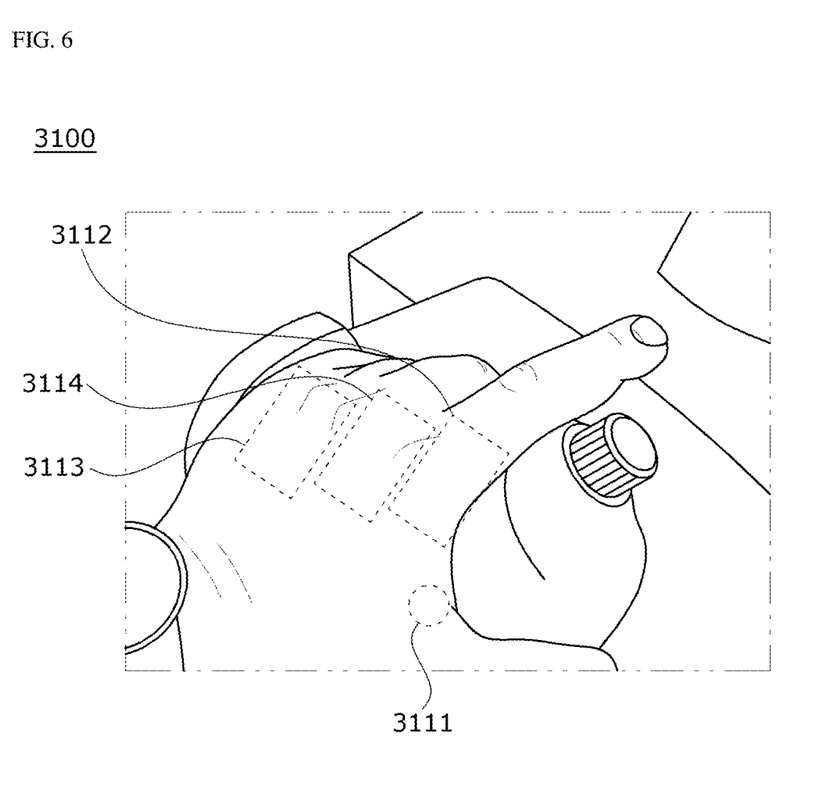
FIG. 6 is a captured image for describing a detection module in contact with a hand of the pilot when the pilot grips the engine thrust control unit according to an embodiment of the present application.

The definitions and the measurement methods for an electrocardiogram, a temperature, a pressure, and a heart rate are the same as those described in the attitude control unit and thus will be omitted. In an example, the engine thrust control unit may have the detection modules 3113, 3114, and 3112 that detect the electrocardiogram, the temperature, and the pressure, which are sequentially provided on the side surface adjacent to the pilot. Further, the detection module (not illustrated) that detects the heart rate may be provided at the lower end of the side surface opposite to the side surface adjacent to the pilot. In detail, FIG. 6 is a captured image for describing a detection module in contact with a hand of the pilot when the pilot grips the engine thrust control unit according to an embodiment of the present application. As illustrated in FIG. 6, the detection modules 3113, 3114, and 3112 that detect the electrocardiogram, the temperature, and the pressure may be sequentially provided at a portion at which the palm of the pilot is positioned when the control stick is gripped. Further, the detection module 3111 that detects the heart rate may be provided at a portion at which a thumb of the pilot is positioned when the control stick is gripped. Accordingly, the health information of the pilot may be continuously monitored, the health information may be collected, and thus flight accidents such as human damages and property damages can be prevented.

The reception modules 1120, 2120, and 3120 are components that receive the biometric information detected by the detection modules. The reception module may receive the biometric information of the pilot acquired from the detection module provided in the military aircraft control stick, for example, the attitude control unit and/or the engine thrust control unit, detect a signal, and generate the biometric information to be transmitted to the flight recorder through the transmission module.

For example, as illustrated in FIGS. 2, 3, and 5, the reception module may be provided adjacent to the detection module that is provided in the attitude control unit or the engine thrust control unit and detects the electrocardiogram.

In an example, the reception module may directly receive a signal generated by the detection module without conversion into a different signal. As the signal generated by the detection module is directly received through the reception module without the conversion into a different signal, addition of a separate signal conversion unit, particularly, an analog/digital (A/D) conversion unit that converts an analog signal into a digital signal, is not required. Thus, an increase in volume can be avoided, the health information of the pilot can be collected in real time, and after the flight, analog data is downloaded to a device on the ground, a health manager present on the ground can continuously monitor the health information of the pilot. Further, the volume increases when the A/D conversion unit is to be mounted on the military aircraft control stick, and thus the A/D conversion unit cannot be mounted on the existing military aircraft.

The transmission modules 1130, 2130, and 3130 are components that transmit the biometric information received by the reception modules to the flight recorder. The transmission modules may transmit the signal detected by the reception modules to the flight recorder. Accordingly, the health information of the pilot may be continuously monitored, the health information may be collected, and thus flight accidents such as human damages and property damages can be prevented.

In an example, the transmission module may include a connection cable that connects the military aircraft control stick to the flight recorder. All types of cables known in the art may be used as the connection cable. As the transmission module increases the connection cable, the biometric information of the pilot may be transmitted to the flight recorder. Accordingly, the health information of the pilot can be continuously monitored, the health information can be collected, and thus flight accidents such as human damages and property damages can be prevented.

For example, the transmission module may transmit the received biometric information to the flight recorder according to a 1553 communication protocol. The 1533 communication protocol is an MIL-STD-1553B protocol that is a communication protocol used for data communication within a military avionics system. That is, as a sensor of the detection module is added to the existing data communication interface, the biometric information received by the reception module may be transmitted to the flight recorder through a 1553 multiplex bus. Accordingly, compatibility can be provided so that the user does not perform separate redesigning when the sensor of the detection module is added to the existing data communication interface.

The flight recorder is a device that automatically records all data related to the aircraft during the flight and may be called a flight data recorder or a black box. For example, as illustrated in FIG. 1, the flight recorder may include a biometric information recording module 1210 that records the transmitted biometric information of the pilot.

As illustrated in FIG. 1, the military aircraft control stick may further include a power module 1140. The power module is a component that applies power to the detection module, the reception module, and the transmission module. The power module may apply power to the detection module, the reception module, and the transmission module to drive the respective modules.

The present application also relates to a health information management system for a pilot. The health information management system relates to the health information management system using the above-described military aircraft control stick. The description of the military aircraft control stick may be equally applied to specific details of the military aircraft control stick, which will be described below, and thus the description thereof will be omitted.

The health information management system for a pilot according to the present application uses the military aircraft control stick. The detailed description of the military aircraft control stick is the same as that described above and thus will be omitted.

The health information management system for a pilot may further include a control glove. Unlike a civil aircraft, in the military aircraft, the pilot should be obliged to wear the control gloves. The control gloves may serve to prevent the pilot from sweating or generating static electricity in a process of operating a navigation system and an electronic device and to protect a hand in a case of emergency. As the health information management system for a pilot further includes the control gloves, the biometric information of the pilot can be transmitted through contact with the control stick even when the pilot wears the control gloves.

Figure 7:
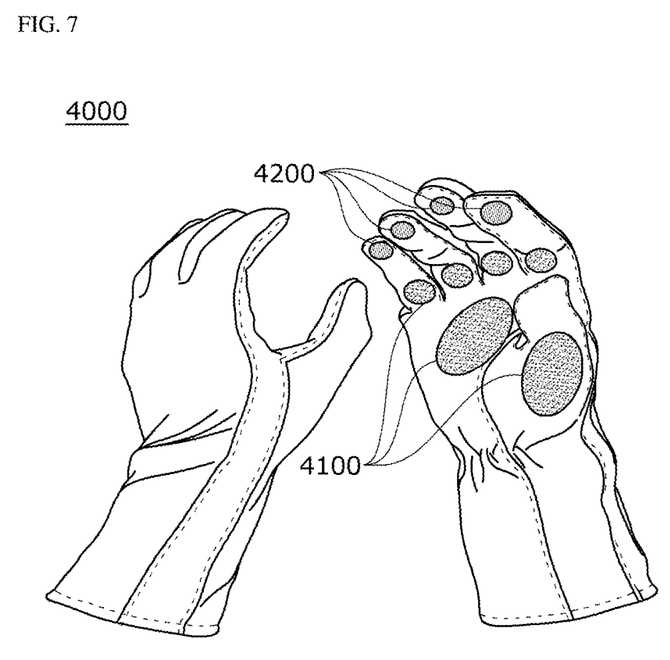
FIG. 7 is a view illustrating a control glove according to an embodiment of the present application.

FIG. 7 is a view illustrating a control glove according to an embodiment of the present application. As illustrated in FIG. 7, the control glove 4000 may have conductive fiber pads 4100 attached thereto. In detail, the conductive fiber pads may be attached to a palm surface of the control glove and knuckle surfaces adjacent to the palm surface. As the conductive fiber pads are attached to the above-described positions of the control glove, a microcurrent may be transmitted through the pilot's skin, and thus the biometric information of the pilot may be transmitted to the detection module of the military aircraft control stick.

In yet another example, the control glove may further have transparent pads 4200 attached thereto. In detail, the transparent pad may be further attached to knuckle surfaces of fingertips of the control glove. The knuckle of the fingertip may be a finger knuckle that is not close to the palm. As the transparent pads are attached to the above-described positions of the control glove, the heart rate can be measured using a blood flow of the finger.

The present application also relates to a military aircraft. The military aircraft relates to a military aircraft including the above-described military aircraft control stick. The description of the military aircraft control stick may be equally applied to specific details of the military aircraft control stick, which will be described below, and thus the description thereof will be omitted.

Figure 8:
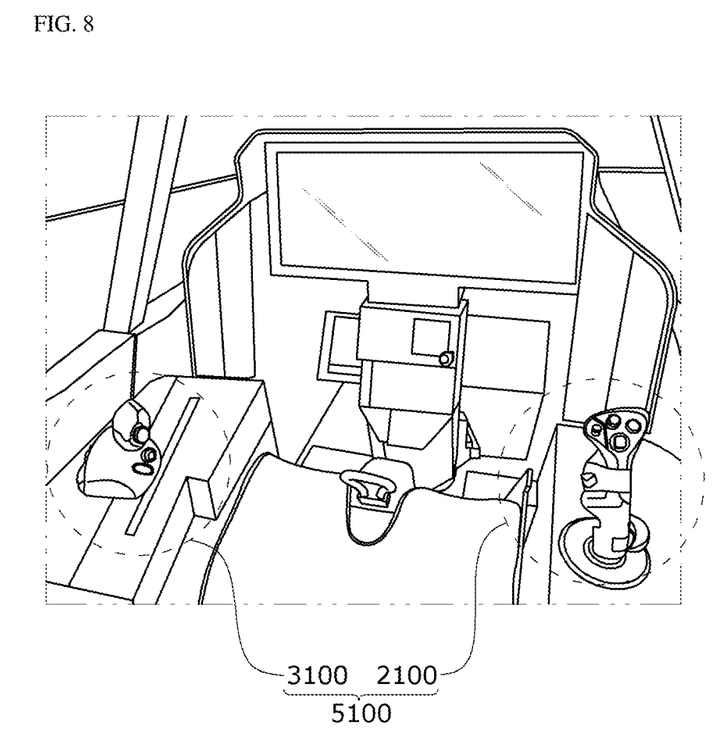
FIG. 8 is a view illustrating an interior of a cockpit of a military aircraft according to an embodiment of the present application.

FIG. 8 is a view illustrating an interior of a cockpit of a military aircraft according to an embodiment of the present application. As illustrated in FIG. 8, the military aircraft includes a military aircraft control stick 5100 described above. The military aircraft control stick may include the attitude control unit 2100 and the engine thrust control unit 3100. The detailed description of the military aircraft control stick is the same as that described above and thus will be omitted. As the military aircraft includes the above-described military aircraft control stick, the health information of the pilot may be acquired when the military aircraft is operated, a health state of the pilot may be continuously monitored and collected by comparing the health information with the health information of the pilot obtained when the military aircraft simulator is operated, and thus flight accidents such as human damages and property damages can be prevented.

The present application also relates to a military aircraft simulator. The military aircraft simulator relates to a military aircraft simulator including the above-described military aircraft control stick. The description of the military aircraft control stick may be equally applied to specific details of the military aircraft control stick, which will be described below, and thus the description thereof will be omitted.

Figure 9:
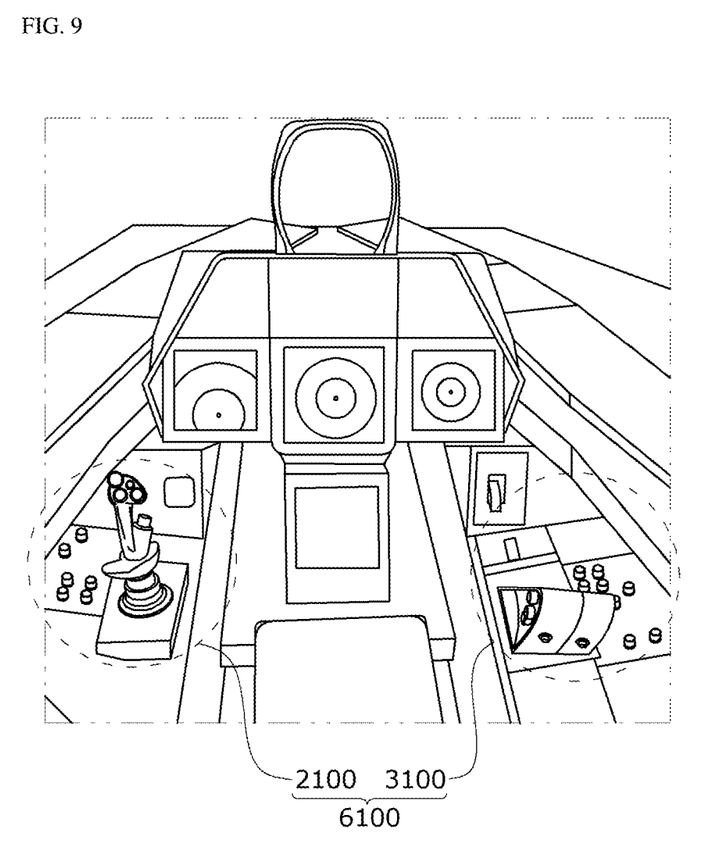
FIG. 9 is a view illustrating an interior of a cockpit of a military aircraft simulator according to an embodiment of the present application.

FIG. 9 is a view illustrating an interior of a cockpit of a military aircraft simulator according to an embodiment of the present application. As illustrated in FIG. 9, the military aircraft simulator includes a military aircraft control stick 6100 described above. The military aircraft control stick may include the attitude control unit 2100 and the engine thrust control unit 3100. The detailed description of the military aircraft control stick is the same as that described above and thus will be omitted. As the military aircraft simulator includes the above-described military aircraft control stick, the health information of the pilot may be acquired when the military aircraft simulator is operated, a health state of the pilot may be continuously monitored and collected by comparing the health information with the health information of the pilot obtained when the military aircraft is operated, and thus flight accidents such as human damages and property damages can be prevented.

DESCRIPTION OF REFERENCE NUMERALS

1100, 5100, 6100: Military aircraft control stick
1110, 2110, 3110: Detection module
1111, 2111, 3111: Detection module that detects heart rate
1112, 2112, 3112: Detection module that detects pressure
1113, 2113, 3113: Detection module that detects electrocardiogram
1114, 2114, 3114: Detection module that detects temperature
1120, 2120, 3120: Reception module
1130, 2130, 3130: Transmission module
1140: Power module
1200: Flight recorder
1210: Biometric information recording module
2100: Attitude control unit
2140: Trim switch
2150: Camera control switch
2160: Armament launch and drop switch
2170: Missile step nosewheel switch
2180: Screen display control switch
2190: Paddle switch
2200: Pinky switch
2210: Target designation or selection switch 2210
2220: Trigger
3100: Engine thrust control unit
3140: Antenna elevation switch
3150: Communication switch
3160: Manual range or uncaging switch
3170: Dog fight or missile switch
4000: Control glove
4100: Conductive fiber pad
4200: Transparent pad

The invention claimed is:

1. A military aircraft control stick comprising:
an attitude control unit; and
an engine thrust control unit,
wherein each of the attitude control unit and the engine thrust control unit includes:
a detection module configured to detect a biometric information of a pilot;
a reception module configured to receive the biometric information detected by the detection module; and
a transmission module configured to transmit the biometric information received by the reception module to a flight recorder.

2. The military aircraft control stick of claim 1, wherein the attitude control unit includes:
a trim switch;
a camera control switch;
an armament launch and drop switch;
a missile step nosewheel switch;
a screen display control switch;
a paddle switch;
a pinky switch;
a target designation or selection switch; and
a trigger.

3. The military aircraft control stick of claim 2, wherein the attitude control unit further includes a detection module configured to detect one or more pieces of biometric information selected from the group consisting of an electrocardiogram and a temperature.

4. The military aircraft control stick of claim 3, wherein, in the attitude control unit, the detection module configured to detect the electrocardiogram is provided at one or more of the trigger and a lower end of a side surface adjacent to the pilot.

5. The military aircraft control stick of claim 4, wherein the reception module is provided adjacent to the detection module provided in the attitude control unit or the engine thrust control unit and configured to detect the electrocardiogram.

6. The military aircraft control stick of claim 3, wherein, in the attitude control unit, a module configured to detect the temperature is provided at an upper end of a side surface adjacent to the pilot.

7. The military aircraft control stick of claim 1, wherein the attitude control unit includes a detection module configured to detect biometric information including a heart rate and a pressure.

8. The military aircraft control stick of claim 7, wherein, in the attitude control unit, the detection module configured to detect the heart rate is provided at a lower end of a side surface opposite to a side surface adjacent to the pilot.

9. The military aircraft control stick of claim 7, wherein, in the attitude control unit, the detection module configured to detect the pressure is provided at a center of a side surface opposite to a side surface adjacent to the pilot.

10. The military aircraft control stick of claim 1, wherein the engine thrust control unit includes:
an antenna elevation switch;
a communication switch;
a speed brake switch;
a manual range or uncaging switch and
a dog fight or missile switch.

11. The military aircraft control stick of claim 1, wherein the engine thrust control unit includes a detection module configured to detect one or more pieces of biometric information selected from the group consisting of an electrocardiogram, a temperature, a pressure, and a heart rate.

12. The military aircraft control stick of claim 11, wherein, in the engine thrust control unit, the detection modules configured to detect the electrocardiogram, the temperature, and the pressure are sequentially provided on a side surface adjacent to the pilot.

13. The military aircraft control stick of claim 11, wherein, in the engine thrust control unit, a detection module configured to detect the heart rate is provided at a lower end of a side surface opposite to a side surface adjacent to the pilot.

14. The military aircraft control stick of claim 1, wherein the reception module directly receives a signal generated by the detection module without conversion into a different signal.

15. The military aircraft control stick of claim 1, wherein the transmission module includes a connection cable configured to connect the military aircraft control stick to the flight recorder.

16. The military aircraft control stick of claim 1, wherein the transmission module transmits the received biometric information to the flight recorder according to a 1553 communication protocol.

17. The military aircraft control stick of claim 1, further including a power module configured to apply power to the detection module, the reception module, and the transmission module.

18. A health information management system for a pilot using the military aircraft control stick according to claim 1.

19. The health information management system of claim 18, further comprising a control glove configured to allow a hand of a pilot to come into direct contact with the military aircraft control stick.

20. The health information management system of claim 19, wherein the control glove has conductive fiber pads attached to a palm surface and a knuckle surface adjacent to the palm surface to transmit a microcurrent of the pilot's skin.

21. The health information management system of claim 20, wherein the control glove further has transparent pads attached to knuckle surfaces of fingertips to measure a heart rate using a blood flow of a finger.

22. A military aircraft including the military aircraft control stick according to claim 1.

23. A military aircraft simulator including the military aircraft control stick according to claim 1.

* * * * *